(12) United States Patent
Sun et al.

(10) Patent No.: US 7,566,412 B2
(45) Date of Patent: *Jul. 28, 2009

(54) DENTAL METHOD AND DEVICE

(75) Inventors: Benjamin J. Sun, York, PA (US);
Andrew M. Lichkus, York, PA (US)

(73) Assignee: DENTSPLY International Inc., York, PA (US)

( * ) Notice: Subject to any disclaimer, the term of this patent is extended or adjusted under 35 U.S.C. 154(b) by 213 days.

This patent is subject to a terminal disclaimer.

(21) Appl. No.: 10/685,652

(22) Filed: Oct. 16, 2003

(65) Prior Publication Data

US 2004/0084792 A1    May 6, 2004

Related U.S. Application Data

(63) Continuation-in-part of application No. 10/405,169, filed on Apr. 2, 2003, which is a continuation-in-part of application No. 10/106,741, filed on Mar. 26, 2002, which is a continuation-in-part of application No. 09/682,440, filed on Sep. 4, 2001, now Pat. No. 6,592,369, which is a continuation-in-part of application No. 09/670,364, filed on Sep. 26, 2000, now abandoned, application No. 10/685,652, which is a continuation-in-part of application No. 10/306,096, filed on Nov. 27, 2002, now Pat. No. 6,799,969, which is a continuation of application No. 09/670,364, filed on Sep. 26, 2000, now abandoned.

(60) Provisional application No. 60/237,523, filed on Oct. 4, 2000, provisional application No. 60/201,705, filed on May 3, 2000, provisional application No. 60/164,893, filed on Nov. 10, 1999.

(51) Int. Cl.
*A61C 13/08* (2006.01)
*A61C 14/09* (2006.01)
*A61C 13/15* (2006.01)

(52) U.S. Cl. .............. 264/19; 264/16; 264/17; 264/20

(58) Field of Classification Search ............. 264/16–17, 264/19–20
See application file for complete search history.

(56) References Cited

U.S. PATENT DOCUMENTS

| | | | | |
|---|---|---|---|---|
| 2,514,075 A * | 7/1950 | Kelly | ................... | 433/203.1 |
| 4,017,971 A | 4/1977 | Hazar | ................... | 32/2 |
| 4,094,067 A | 6/1978 | Hazar | ................... | 32/2 |
| 4,097,992 A | 7/1978 | Hazar | ................... | 32/2 |
| 4,133,110 A | 1/1979 | Bernstein et al. | ................... | 32/2 |
| 4,161,065 A | 7/1979 | Gigante | ................... | 32/2 |
| 4,175,322 A | 11/1979 | Tureaud | ................... | 433/171 |
| 4,247,287 A | 1/1981 | Gigante | ................... | 433/199 |
| 4,248,807 A | 2/1981 | Gigante | ................... | 264/18 |
| 4,259,074 A | 3/1981 | Link | ................... | 433/214 |
| 4,345,900 A | 8/1982 | Katz et al. | ................... | 433/171 |
| 4,375,966 A | 3/1983 | Freeman | ................... | 433/37 |
| 4,452,964 A * | 6/1984 | Saracsan | ................... | 528/75 |
| 4,457,818 A | 7/1984 | Denyer et al. | ................... | 204/159 |
| 4,543,063 A | 9/1985 | Cohen | ................... | 433/175 |
| 4,551,098 A | 11/1985 | Blair | ................... | 433/171 |
| 4,609,351 A | 9/1986 | Blair | ................... | 433/55 |
| 4,705,476 A | 11/1987 | Blair | ................... | 433/171 |
| 4,721,735 A | 1/1988 | Bennett et al. | ................... | 522/71 |
| 4,813,875 A | 3/1989 | Hare | ................... | 433/214 |
| 4,978,298 A | 12/1990 | Eliasz | ................... | 433/213 |
| 5,037,294 A * | 8/1991 | Bergersen | ................... | 433/6 |
| 5,057,259 A * | 10/1991 | Parmelee | ................... | 264/166 |
| 5,063,255 A | 11/1991 | Hasegawa et al. | ................... | 522/96 |
| 5,167,781 A * | 12/1992 | Kemerer et al. | ................... | 264/166 |
| 5,177,120 A | 1/1993 | Hare et al. | ................... | 433/37 |
| 5,213,498 A | 5/1993 | Pelerin | ................... | 433/37 |
| 5,304,063 A | 4/1994 | Ginsburg | ................... | 433/199 |
| 5,348,475 A * | 9/1994 | Waknine et al. | ................... | 433/215 |
| 5,403,186 A | 4/1995 | Ginsburg | ................... | 433/199 |
| 5,591,786 A | 1/1997 | Oxman et al. | ................... | 533/109 |
| 5,635,545 A | 6/1997 | Oxman et al. | ................... | 523/115 |
| 5,672,305 A * | 9/1997 | Kogure | ................... | 264/102 |
| 5,710,194 A * | 1/1998 | Hammesfahr et al. | ................... | 523/116 |
| 5,711,668 A | 1/1998 | Huestis | ................... | 433/167 |
| 5,993,208 A | 11/1999 | Jonjic | ................... | 433/50 |
| 6,031,015 A | 2/2000 | Ritter et al. | ................... | 522/77 |
| 6,057,383 A | 5/2000 | Volkel et al. | ................... | 523/116 |
| 6,121,344 A * | 9/2000 | Angeletakis et al. | ................... | 523/116 |
| 6,136,886 A * | 10/2000 | Deguchi | ................... | 523/116 |
| 6,174,168 B1 | 1/2001 | Dehoff et al. | ................... | 433/202.1 |
| 6,244,864 B1 | 6/2001 | Fujiwara et al. | ................... | 433/71 |
| 6,384,107 B2 * | 5/2002 | Liu | ................... | 523/118 |
| 6,387,981 B1 | 5/2002 | Zhang et al. | ................... | 523/117 |
| 6,921,500 B1 * | 7/2005 | Feenstra | ................... | 264/19 |
| 2003/0113689 A1 | 6/2003 | Sun et al. | | |
| 2003/0190585 A1 | 10/2003 | Sun et al. | | |

FOREIGN PATENT DOCUMENTS

| | | |
|---|---|---|
| EP | 0 630 640 | 12/1994 |
| EP | 813 856 | 6/1997 |
| EP | 1 042 994 | 9/1999 |
| GB | 2 225 333 | 5/1990 |

* cited by examiner

*Primary Examiner*—Matthew J. Daniels
(74) *Attorney, Agent, or Firm*—Douglas J. Hura

(57) ABSTRACT

A dental device and method of making it, by shaping a first and a second wax-like polymerizable dental material to form a polymerizable dental device.

5 Claims, No Drawings

DENTAL METHOD AND DEVICE

This application is a continuation-in-part of U.S. patent application Ser. No. 10/405,169 filed Apr. 2, 2003 (pending), which is a continuation-in-part of U.S. patent application Ser. No. 10/106,741 filed Mar. 26, 2002 (pending) which is a continuation-in-part of U.S. patent application Ser. No. 09/682,440 filed Sep. 4, 2001 (now U.S. Pat. No. 6,592,369 B2) which is a continuation-in-part of U.S. patent application Ser. No. 09/670,364 filed Sep. 26, 2000, (abandoned). This application is a continuation-in-part of U.S. patent application Ser. No. 10/306,096 filed Nov. 27, 2002 now U.S. Pat. No. 6,799,969 which is a continuation of U.S. patent application Ser. No. 09/670,364 filed Sep. 26, 2000, (abandoned). The benefit is claimed of US provisional patent application Ser. No. 60/237,523 filed Oct. 4, 2000, U.S. Provisional Patent Application Ser. No. 60/201,705 filed May 3, 2000, and U.S. Provisional Patent Application Ser. No. 60/164,893 filed Nov. 10, 1999.

A dental device and method of making it, by shaping a first and a second wax-like polymerizable dental material to form a polymerizable dental device.

DETAILED DESCRIPTION OF THE INVENTION

Compositions useful in accordance with the invention may further include fillers, pigments, stabilizers, plasticizers and fibers. Preferably, these polymerizable dental compositions include from about 2 to about 95 percent by weight filler particles. More preferably, these compositions include from about 10 to about 85 percent by weight filler. Nanocomposites and creamers may be formed from these composites. The fillers preferably include both organic and inorganic particulate fillers to further reduce polymerization shrinkage, improve wear resistance and modify the mechanical and physical properties.

Light curable polymerizable dental materials preferably include a light sensitizer, for example camphorquinone, Lucirin TPO, or methyl benzoin which causes polymerization to be initiated upon exposure to activating wavelengths of light; and/or a reducing compound, for example tertiary amine. A room temperature or heat activating catalyst system is preferably included in the polymerizable dental material. For example a peroxide capable of producing free radicals when activated by a reducing agent at room temperature or by heating. Preferred peroxides include benzyl peroxide and lauroyl peroxide.

A preferred embodiment of the invention uses a high strength dental polymeric material formed by light curing polymerizable dental material shaped into at least a portion of a denture base or tooth. Preferably the polymerizable dental material has a flexural modulus of at least 250,000 psi and a flexural strength of at least 7,000 psi. Preferably a denture of the invention comprises a denture base and a tooth integrally connected and comprising an interpenetrating polymer network polymeric matrix and at least 0.1 percent by weight of self-lubricating particles having a particle size less than 500 microns effectively bonded to and distributed in the polymeric matrix. Preferably the integral connection of the denture base and a tooth is effectively greater than a bond strength of 4,480 psi.

"Wax-like material" as used herein refers to material which is flowable (fluid) above 40° C. and becomes dimensionally stable (solidifies: i.e. is nonfluid) at least at and below 23° C., within 5 minutes. Thus, wax-like material is flowable when it is at and above 40° C., and becomes dimensionally stable when it is at and below 23° C. Flowable wax-like material having a temperature from 100° C. to 40° C., becomes dimensionally stable within 5 minutes by cooling by exposure to an ambient temperature between 23° C. and 0° C. Flowable wax-like material having a temperature from 100° C. to 40.° C., becomes dimensionally stable within (in order of increasing preference) 2, 1, 0.5 or 0.3 minutes by cooling by exposure to an ambient temperature between 23° C. and 0° C.

"High strength dental polymeric material" as used herein refers to material having a polymeric matrix having a flexural modulus of at least 250,000 psi and a flexural strength of at least 5,000 psi. Optionally, high strength dental polymeric material includes reinforcing filler. However, the polymeric matrix alone (without any reinforcing filler) has a flexural modulus of at least 250,000 psi and a flexural strength of at least 5,000 psi. Preferably high strength dental polymeric material has a polymeric matrix having a flexural modulus of at least 300,000 psi and a flexural strength of at least 7,000 psi. More preferably high strength dental polymeric material in order of increasing preference has a polymeric matrix having a flexural modulus of at least 350,000 psi and a flexural strength of at least 12,000 psi. Artificial teeth and denture base both made of high strength dental polymeric material are integrally connected in dental products including full dentures, partial dentures and bridges during polymerization of polymerizable dental material.

"Flexural strength, and flexural modulus" as used herein refers to results of testing according to ASTM D790 (1997). "Notched impact strength" as used herein is also referred to as "notched Izod impact resistance" and refers to results of testing according to ASTM D256 (1997). "Un-notched impact strength" as used herein refers to results of testing according to ASTM D4812 (1993).

In the following examples, unless otherwise indicated, all parts and percentages are by weight; Lucirin TPO refers to 2,4,6-trimethylbenzoyldiphenylphosphine oxide made by BASF, and the visible light curing unit used was an Eclipse visible light curing unit, sold by Dentsply International, providing about 30 milliwatts/cm$^2$ of from 350 to 450 nm light.

Preparation 1

Preparation of Oligomer

A reactor was charged with 1176 grams of trimethyl-1,6-diisocyanatohexane (5.59 mol) and 1064 grams of bisphenol A propoxylate (3.09 mol) under dry nitrogen flow and heated to about 65° C. under a positive nitrogen pressure. To this reaction mixture, 10 drops of catalyst dibutyltin dilaurate were added. The temperature of the reaction mixture was maintained between 65° C. and 140° C. for about 70 minutes and followed by additional 10 drops of catalyst dibutyltin dilaurate. A viscous paste-like isocyanate end-capped intermediate product was formed and stirred for 100 minutes.

To this intermediate product, 662 grams (5.09 mol) of 2-hydroxyethyl methacrylate and 7.0 grams of BHT as an inhibitor were added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

Preparation 2

Preparation of Monomer

A reaction flask was charged with 700 grams of 1,6-diisocyanatohexane and heated to about 70° C. under a positive nitrogen pressure. To this reactor were added 1027 grams of 2-hydroxyethyl methacrylate, 0.75 gram of catalyst dibutyltin dilaurate and 4.5 grams of butylated hydroxy toluene (BHT). The addition was slow and under dry nitrogen flow over a period of two hours. The temperature of the reaction mixture was maintained between 70° C. and 90° C. for another two hours and followed by the addition of 8.5 grams of purified water. One hour later, the reaction product was discharged as clear liquid into plastic containers and cooled to form a white solid and stored in a dry atmosphere.

Preparation 3

Preparation of Polymerizable Denture Base Plate Material

A light curable polymerizable material was prepared by stirring at 85° C. a liquid of 98.0 grams of TBDMA oligomer of Preparation 1, 0.35 gram of 2,4,6-trimethylbenzoyldiphenylphosphine oxide, (Lucirin TPO made by BASF), 1.5 gram of solution containing 8.3% camphorquinone (CQ), 25% ethyl 4-dimethylaminobenzoate (EDAB) and 66.7% 1,6-hexanediol dimethacrylate (HDDMA), 0.1 gram of red acetate fibers and 0.05 gram of pigment.

Preparation 4

Preparation of Polymerizable Wax-Like Denture Contour Material

A light curable wax-like polymerizable dental material was prepared by stirring at 85° C. a liquid mixture of 50.5 grams of oligomer of Preparation 1, 45.0 grams of monomer of Preparation 2 and 4.0 grams of stearyl acrylate from Sartomer. To this mixture were added 0.35 gram of 2,4,6-trimethylbenzoyldiphenylphosphine oxide (Lucirin TPO), 0.1 gram of red acetate fibers and 0.05 gram of pigment concentrates. The polymerizable wax-like material formed becomes flowable at 65 to 68° C.

Preparation 5

Preparation of Polymerizable Denture Set-up Material

A light curable polymerizable material was prepared by stirring at 85° C. a liquid mixture of 84.5 grams of oligomer of Preparation 1 and 15.0 grams of monomer of Preparation 2. To this mixture, 0.35 gram of 2,4,6-trimethylbenzoyldiphenylphosphine oxide (Lucirin TPO), 0.1 gram of red acetate fibers and 0.05 gram of pigment were added.

Preparation 6

Preparation of Polymerizable Wax-like Artificial Tooth Resin

A light curable wax-like polymerizable dental material was prepared by stirring at 85° C. a liquid mixture of 50 grams of oligomer of Preparation 1, 30.0 grams of monomer of Preparation 2 and 20 grams of monomer of Preparation 2. To this mixture were added 0.35 gram of 2,4,6-trimethylbenzoyldiphenylphosphine oxide (Lucirin TPO), and 0.05 gram of pigment concentrates. The polymerizable wax-like material formed becomes flowable at 65 to 70° C.

Preparation 7

Preparation of Monomer

A reaction flask was charged with 168 grams of 1,6-diisocyanatohexane and heated to about 70° C. under a positive nitrogen pressure. To this reactor were added 228 grams of 2-hydroxyethyl acrylate, 0.12 gram of catalyst dibutyltin dilaurate and 0.86 grams of butylated hydroxy toluene (BHT). The addition was slow and under dry nitrogen flow over a period of two hours. The temperature of the reaction mixture was maintained between 70° C. and 85° C. for another three hours and followed by the addition of 0.9 grams of purified water. One hour later, the reaction product was discharged as clear liquid into plastic containers and cooled to form a white solid and stored in a dry atmosphere.

Preparation 8

Preparation of Monomer

A reaction flask was charged with 47.7 grams of p-tolyl isocyanate and heated to about 46° C. under a positive nitrogen pressure. To this reactor were added 48.13 grams of 2-hydroxyethy methacrylate, 0.06 gram of catalyst dibutyltin dilaurate and 0.30 grams of butylated hydroxy toluene (BHT). The addition was under dry nitrogen flow over a period of 40 minutes while the temperature of the reaction mixture was raised to 78° C. and maintained between 72° C. and 78° C. for another 1.3 hours. The reaction product was discharged as clear liquid into a plastic container and cooled to form a semi-opaque off white solid and stored in a dry atmosphere.

EXAMPLES 1A and 1B

Table 1 shows the components and Table 2 shows the properties of the compositions of Examples 1A through 1B. The compositions of Examples 1A through 1B were prepared by mixing the components shown in Table 1 at 95° C.

TABLE I

|  | Example 1A (grams) | Example 1B (grams) |
| --- | --- | --- |
| Titanium dioxide | 0.385 | 0 |
| Iron oxide | 0.0499 | 0.002 |
| Red-Brown Pigment Blend | 0.0132 | 0.0012 |
| Ultramarine Blue Pigment | 0 | 0.0028 |
| Black Dry Color Blend | 0.0134 | 0 |
| a blend of 82.99% ZnO, 16.18% Magnesium carbonate, 0.62% Lithium sulfate and 0.21% Sulfur, (sublimed powder). [115 Phosphor] | 0.194 | 0.05 |
| dihydroxy terepthalate acid ester [FLU-L-BLU] | 0.08 | 0.024 |
| Monomer of Preparation 2 | 40.4 | 17.2 |
| Monomer of Preparation 7 | 28.0 | 24.6 |
| Monomer of Preparation 8 |  | 24.6 |
| Oligomer of Preparation 1 | 68.16 | 41.6 |
| Lucirin TPO | 0.6 | 0.32 |
| Camphorquinone | 0.32 | 0.212 |
| N, N-dimethyl-aminoneopentyl acrylate | 1.11 | 0.74 |
| Methacrylic Acid | 0.55 | 0.368 |
| Butylated Hydroxytoluene | 0.03 | 0.02 |
| γ-methacryloxypropyl-silane | 0.39 | 0.26 |
| silanated fumed silica*** (SiO$_2$) | 28.54 | 6 |
| silanated barium aluminoflurosilicate glass (BAFG)** | 228.39 | 168 |
| silanated barium aluminoflurosilicate glass (BAFG)* | 114.19 | 116 |

*Barium glass particles having an average particle size of from about 1 to about 10 micrometers.
**Barium glass particles having an average particle size of from about 0.1 to about 1 micrometers.
***Fumed silica having an average particles size of from about 0.01 to about 0.04 micrometers.

The physical properties of the material of Examples 1A and 1B were tested and results listed in Table 2:

TABLE 2

| Property | Example 1A | Example 1B |
| --- | --- | --- |
| Localized Wear - mm$^3$ | 0.021 |  |
| Flexural Strength - psi | 19,600 | 17,330 |
| Flexural Modulus - kpsi | 1,625 | 1,580 |

TABLE 2-continued

| Property | Example 1A | Example 1B |
|---|---|---|
| Compressive Strength - MPa | 358** | |
| Water Sorption - µg/mm$^3$ | 14.9 | |

**Compressive Strength was measured using 50 kN load cell set to run at 2,000 pounds with crosshead speed at 2 inches (50.8 mm)/per minute. Compressive strength testing specimens were prepared by following the procedure of U.S. Pat. No. 6,387,981. Each composite was packed into a 4 mm inside diameter glass tube, capped with silicone rubber plugs and axially compressed at about 0.28 MPa for 15 minutes, then light cured for 10 minutes in Eclipse light curing unit (voltage at 37.5 V, blowers at 80 percent). Cured samples were cut on a diamond saw to form cylindrical plugs 8 mm long and stored in distilled water at 37° C. for 24 hours and then measured for compressive strength.

A three body cyclic abrasion wear machine (Leinfelder/University of Alabama in vitro) was used to determine volume loss (cubic mm at 400,000 cycles), as a measure of the wear resistance of the polymerized composite compositions of Examples 1A and 1B.

Water sorption of the polymerized composite compositions of Examples 1A and 1B was measured according to ISO 4049. The samples were cured for 10 minutes in the Eclipse light curing unit (voltage at 37.5 V, blowers at 80% from 5:30-10:00 minutes).

Flexural Strength and Flexural Modulus of the polymerized composite compositions of Examples 1A and 1B were measured by using three-point bend test on Instron bending unit according to ASTM D790 (1997). Samples were cured in metal molds in an Eclipse light curing unit for 10 minutes (voltage at 37.5 V, blowers at 80% from 5.5-10 minutes).

The composition of Example 1A is dimensionally stable below 60° C., begins to soften at 60° C. and becomes flowable as it is heated less than 1 degree above 70° C. The composition of Example 1B is dimensionally stable below 57° C., begins to soften at 57° C. and becomes flowable as it is heated less than 1 degree above 67° C.

EXAMPLE 2

Continuous Tooth Making

Two steel disks each has a cylindrical outer face with a sequence of tooth mold halves therein. The two steel disks are rotated so that they are in contact along their outer cylindrical faces. The corresponding tooth mold halves on each disk are aligned while their portions of the cylindrical outer faces are in the contact. A sheet of polymerizable wax-like material at 60° C., formed by following the procedure of Preparation 6, is continuously fed between the aligning outer faces of the two rotating steel disks, each at 37° C. The corresponding tooth mold halves on each disk shape 0.5 g to 2 g portions of the polymerizable wax-like material into artificial teeth as they rotate into alignment with each other.

EXAMPLE 3

Multiple Layered Tooth Making

Each of two steel mold halves has fourteen half tooth molds therein. The two steel mold halves (each at 37° C.) are positioned in contact, with the corresponding half tooth molds aligned, and a sheet of polymerizable wax-like composite material (at 60° C.) positioned between the aligned faces of the two mold halves. The polymerizable wax-like composite material is formed by following the procedure of Example 1B. The corresponding tooth mold halves shape 0.3 g portions of the polymerizable wax-like composite material into each of the enamels of artificial teeth as they are aligned with each other. One steel mold half (without enamels of artificial teeth) is removed and an additional steel mold half (at 37° C.) applied in its place, so that the mold halves are in contact along their mold outer faces. The additional steel mold also has fourteen half tooth molds therein. A sheet of polymerizable wax-like composite material at 60° C., formed by following the procedure of Example 1A, is positioned between the two mold halves. The polymerizable wax-like composite material is forced into the tooth mold cavities. The corresponding tooth mold halves shape 1 g portions of the polymerizable wax-like composite material (at 60° C.) into each of the artificial tooth bodies. Each artificial tooth body combines with the enamel in its mold cavity to form a two layer artificial tooth.

The fourteen teeth formed are positioned into a molded denture base of material prepared by following the procedure of Preparation 3, and light cured by impinging light thereon for 60 seconds from a Spectrum 800 light curing unit (sold by Dentsply International Inc), followed by curing for 10 minutes in a Triad 2000 light curing unit (sold by Dentsply International Inc). The adjacent surfaces of the teeth and the denture base combine during polymerization to form an integral denture.

EXAMPLE 4

Continuous Multiple Layered Tooth Making

Each of two steel disks has a sequence of fourteen half teeth molds in its cylindrical outer face. The two steel disks (each at 37° C.) are rotated so that they are in contact along their outer cylindrical faces, with the corresponding half tooth molds aligned, as a sheet of polymerizable wax-like composite material (at 60° C.) continuously fed between the aligned faces of the two disks. The polymerizable wax-like composite material is formed by following the procedure of Example 1B. The corresponding tooth mold halves shape 0.3 g portions of the polymerizable wax-like composite material into each of the enamels of artificial teeth as they are rotated into alignment with each other. One steel disk without enamels of artificial teeth is removed and an additional steel disk (at 37° C.) put in its place, so that the mold halves are in contact along their mold outer faces as they are rotated. The additional steel disk also has fourteen half tooth molds therein. A sheet of polymerizable wax-like composite material at 60° C., formed by following the procedure of Example 1A, is continuously fed between the two disks. The polymerizable wax-like composite material is forced into the tooth mold cavities. The corresponding tooth mold halves shape 1 g portions of the polymerizable wax-like composite material (at 60° C.) into artificial tooth bodies. Each artificial tooth body combines with the enamel in its mold cavity to form a two layer artificial tooth.

The fourteen teeth formed are positioned into a molded denture base of material prepared by following the procedure of Preparation 4, and light cured by impinging light thereon for 10 minutes in an Eclipse light curing unit, sold by Dentsply International Inc. The adjacent surfaces of the teeth and the denture base combine during polymerization to form an integral denture.

EXAMPLE 5

Multiple Layered Crown

Each of two steel mold halves has fourteen half crown molds therein. The two steel mold halves (each at 37° C.) are positioned in contact, with the corresponding half crown molds aligned, and a sheet of polymerizable wax-like composite material (at 60° C.) positioned between the aligned faces of the two mold halves. The polymerizable wax-like composite material is formed by following the procedure of Example 1B. The corresponding tooth mold halves shape 0.3 g portions of the polymerizable wax-like composite material into each of the enamels of crowns as they are aligned with each other. One steel mold half (without enamels of crowns) is removed and an additional steel mold half (at 37° C.) applied in its place, so that the mold halves are in contact along their mold outer faces. The additional steel mold also has fourteen half tooth molds therein. A sheet of polymerizable wax-like composite material at 60° C., formed by following the procedure of Example 1A, is positioned between the two mold halves. The polymerizable wax-like composite material is forced into the crown mold cavities. The corresponding crown mold halves shape 1 g portions of the polymerizable wax-like composite material (at 60° C.) into each of the crown bodies. Each crown body combines with the enamel in its mold cavity to form a two layer crown.

In use the bottom of the body of a crown is warmed to soften it. The crown is pressed and positioned onto a tooth prepared by cutting and applying adhesive. The softened portion of the crown conforms to the upper face of the prepared tooth. The enamel portion of the crown retains its shape. The positioned crown is then light cured.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A method of making a multi-layered dental device, comprising the steps of: shaping a first wax-like polymerizable dental material, said first material being dimensionally stable in its uncured state at ambient temperature and comprising a mixture of monomer, oligomer, and light sensitizer and optionally including reinforcing filler, to form a first portion of a polymerizable dental device, shaping a second wax-like polymerizable dental material, said second material being dimensionally stable in its uncured state at ambient temperature and comprising a mixture of monomer, oligomer, and light sensitizer and optionally including reinforcing filler, to form a second portion of said polymerizable dental device, and polymerizing said first and second dental materials by light-curing after both materials have been applied to form a multi-layered dental device having a polymeric matrix, which alone, has a flexural modulus of at least 250,000 psi and a flexural strength of at least 5,000 psi.

2. The method of claim 1 wherein said first wax-like polymerizable dental material has a first flowable temperature, said second wax-like polymerizable dental material has a second flowable temperature, and said first flowable temperature, is effectively higher than said second flowable temperature.

3. The method of claim 1 wherein said polymerizable dental device is selected from the group consisting of artificial tooth, bridge, full denture, and partial denture.

4. The method of claim 1 wherein said first wax-like polymerizable dental material is shaped into a tooth enamel.

5. The method of claim 1 wherein at least one of said first and said second wax-like polymerizable dental material comprises reinforcing filler.

* * * * *